United States Patent
Jin et al.

(10) Patent No.: US 9,799,498 B2
(45) Date of Patent: Oct. 24, 2017

(54) MAGNETRON SPUTTERING COATING DEVICE, A NANO-MULTILAYER FILM, AND THE PREPARATION METHOD THEREOF

(71) Applicant: ZhongAo HuiCheng Technology Co., Ltd., Beijing (CN)

(72) Inventors: Gong Jin, Beijing (CN); Jiangping Tu, Beijing (CN); Lingling Li, Beijing (CN); Gang Wang, Beijing (CN); Meina Wang, Beijing (CN)

(73) Assignee: ZhongAo HuiCheng Technology Co., Ltd., Beijing (CN)

( * ) Notice: Subject to any disclaimer, the term of this patent is extended or adjusted under 35 U.S.C. 154(b) by 238 days.

(21) Appl. No.: 14/704,197

(22) Filed: May 5, 2015

(65) Prior Publication Data

US 2015/0235818 A1 Aug. 20, 2015

Related U.S. Application Data

(62) Division of application No. 13/891,309, filed on May 10, 2013.

(30) Foreign Application Priority Data

May 15, 2012 (CN) .......................... 2012 1 0151152
May 15, 2012 (CN) ...................... 2012 2 0218296 U

(51) Int. Cl.
*H01J 37/34* (2006.01)
*C23C 14/00* (2006.01)

(52) U.S. Cl.
CPC ...... *H01J 37/3417* (2013.01); *H01J 37/3429* (2013.01); *H01J 37/3447* (2013.01); *H01J 37/3411* (2013.01)

(58) Field of Classification Search
CPC .......................... H01J 37/3411; H01J 37/3447
See application file for complete search history.

(56) References Cited

U.S. PATENT DOCUMENTS 6,143,149 A * 11/2000 Abe .................... C23C 14/3407
204/192.12
6,562,445 B2    5/2003 Iwamura
(Continued)

FOREIGN PATENT DOCUMENTS

CN    201660695 U    12/2010
JP    11-100671    4/1999
(Continued)

OTHER PUBLICATIONS

Voevodin et al., "Design of a Ti/TiC/DLC functionality gradient coating based on studies of structural transitions in Ti—C thin films" *Thin Solid Films*, vol. 298, 1997, p. 107-115.
(Continued)

*Primary Examiner* — Timon Wanga

(57) ABSTRACT

A magnetron sputtering coating device includes a deposition chamber, sputtering cathodes, a rotating stand within the deposition chamber, a support platform on the rotating stand, a first rotation system for driving the rotating stand to rotate around a central axis of the rotating stand, and a baffle fixed on the rotating stand. The sputtering cathodes are arranged around and perpendicular to the rotating stand.

10 Claims, 3 Drawing Sheets

(56) References Cited

U.S. PATENT DOCUMENTS

| | | | |
|---|---|---|---|
| 6,740,393 B1 | 5/2004 | Massler et al. | |
| 7,820,293 B2 | 10/2010 | Dekempeneer | |
| 2004/0038033 A1* | 2/2004 | Massler | C23C 16/029 |
| | | | 428/408 |
| 2005/0199490 A1* | 9/2005 | Nomura | C23C 14/3464 |
| | | | 204/298.11 |
| 2006/0188660 A1* | 8/2006 | Teer | C23C 14/352 |
| | | | 427/524 |
| 2009/0211897 A1* | 8/2009 | Tsunekawa | C23C 14/165 |
| | | | 204/192.13 |
| 2010/0000855 A1* | 1/2010 | Nakamura | C23C 14/225 |
| | | | 204/192.12 |
| 2011/0030794 A1* | 2/2011 | Teng | C23C 14/0623 |
| | | | 136/262 |
| 2013/0309486 A1 | 11/2013 | Jin et al. | |
| 2014/0110253 A1* | 4/2014 | Tamagaki | C23C 16/509 |
| | | | 204/298.06 |

FOREIGN PATENT DOCUMENTS

| | | | |
|---|---|---|---|
| JP | 2002-322555 | | 11/2002 |
| JP | 2008-081630 | | 4/2008 |
| JP | 2011-184819 | * | 8/2011 |

OTHER PUBLICATIONS

Non-final Office Action dated Dec. 18, 2014, issued in corresponding U.S. Appl. No. 13/891,309, (6 pages).

* cited by examiner

MAGNETRON SPUTTERING COATING DEVICE, A NANO-MULTILAYER FILM, AND THE PREPARATION METHOD THEREOF

CROSS REFERENCE OF RELATED APPLICATIONS

The present application is a divisional application of U.S. patent application Ser. No. 13/891,309, filed May 10, 2013, which claims the benefit of Chinese Patent Application No. 201210151152.2, filed on May 15, 2012, and Chinese Patent Application No. 201220218296.0, filed on May 15, 2012. All of the above-referenced applications are incorporated by reference in their entirety.

TECHNICAL FIELD

The present invention relates to a material preparation field, particularly to a device for preparation of a nano-multilayer film, a nano-multilayer film and the preparation method thereof.

BACKGROUND

Vacuum magnetron sputtering technology has been widely used for coating surfaces of substrates. For example, such technology can be used for coating such as diamond-like carbon (DLC) material on surfaces of medical surgical equipment, human implantation medical materials, and engineering tools. The coating will significantly increase hardness and wear resistance of the substrate.

Because a diamond-like carbon material has a large internal stress, and does not have a high binding force with metal or alloy materials, it is prone to rupture or peeling under a high load or load impact. In particular, if such coatings are used on a human implantation product, the peeling of diamond-like carbon may produce debris, which will aggravate the wear of the implantation product and reduce the service life of the product.

In order to resolve the above problems, the present disclosure provides a nano-multilayer film, which can increase the wear resistance of the substrate, increase the binding force with the substrate, and improve lubricity.

SUMMARY

The present disclosure provides a magnetron sputtering coating device. According to some embodiments, the magnetron sputtering coating device includes a deposition chamber, a rotating stand positioned within the deposition chamber and having a rotating axis, two first sputtering cathodes and a second sputtering cathode located on a circumference concentric with the rotating axis. The second sputtering cathode contains a material different from the two first sputtering cathodes. The magnetron sputtering coating device may further include a baffle fixed on the rotating stand and divides the deposition chamber into at least two areas. The baffle separate at least one first sputtering cathode into one area, and the second sputtering cathode into another area.

The present disclosure also provides a method for preparing a multilayer film on a substrate. According to some embodiments, the method for preparing a multilayer film on a substrate includes providing at least one first sputtering cathode in a deposition chamber, providing at least one second sputtering cathode in the deposition chamber. The second sputtering cathode includes a sputtering material that is different from the first sputtering cathode. The method may further includes providing a first current to the at least one first sputtering cathode for sputtering the substrate, and increasing the first current gradually, providing a second current to the at least one second sputtering cathode for sputtering the substrate and decreasing the second current gradually, and rotating the substrate within the deposition chamber to alternatively sputter the substrate with the at least one first sputtering cathode or the at least one second sputtering cathode.

The present disclosure further provides a multilayer film prepared by magnetron sputtering coating. According to some embodiments, the multilayer film prepared by magnetron sputtering coating includes a transition layer on a substrate. The transition layer includes a titanium layer and a mixed layer of titanium carbide and quasi-graphite on the titanium layer. The multilayer film may further includes a composite layer on the transition layer. The composite layer includes a multilayer structure with a quasi-graphite layer and a diamond-like carbon layer alternately laminated. The quasi-graphite layer includes 60% of materials by mass with a sp2 bond and the diamond-like carbon layer includes 70% of materials by mass with a sp3 bond. The multilayer film may further includes a diamond-like carbon layer on the composite layer. In the multilayer film, in a direction from the substrate to the diamond-like carbon layer, the mass percentage of titanium in the mixed layer of titanium carbide and quasi-graphite is gradually decreased, while the mass percentage of carbon is gradually increased.

BRIEF DESCRIPTIONS OF THE DRAWINGS

The above and/or additional aspects and advantages of the present invention will become obvious and comprehensible from the following description of the examples with reference to the drawings.

DETAILED DESCRIPTION OF EMBODIMENTS

For better understanding the technical solution and beneficial effects of the present invention, the examples of the present invention will be described in detail below. The examples described below with reference to the drawings are exemplary only for explanation rather than restriction of the present invention.

Figure 1:
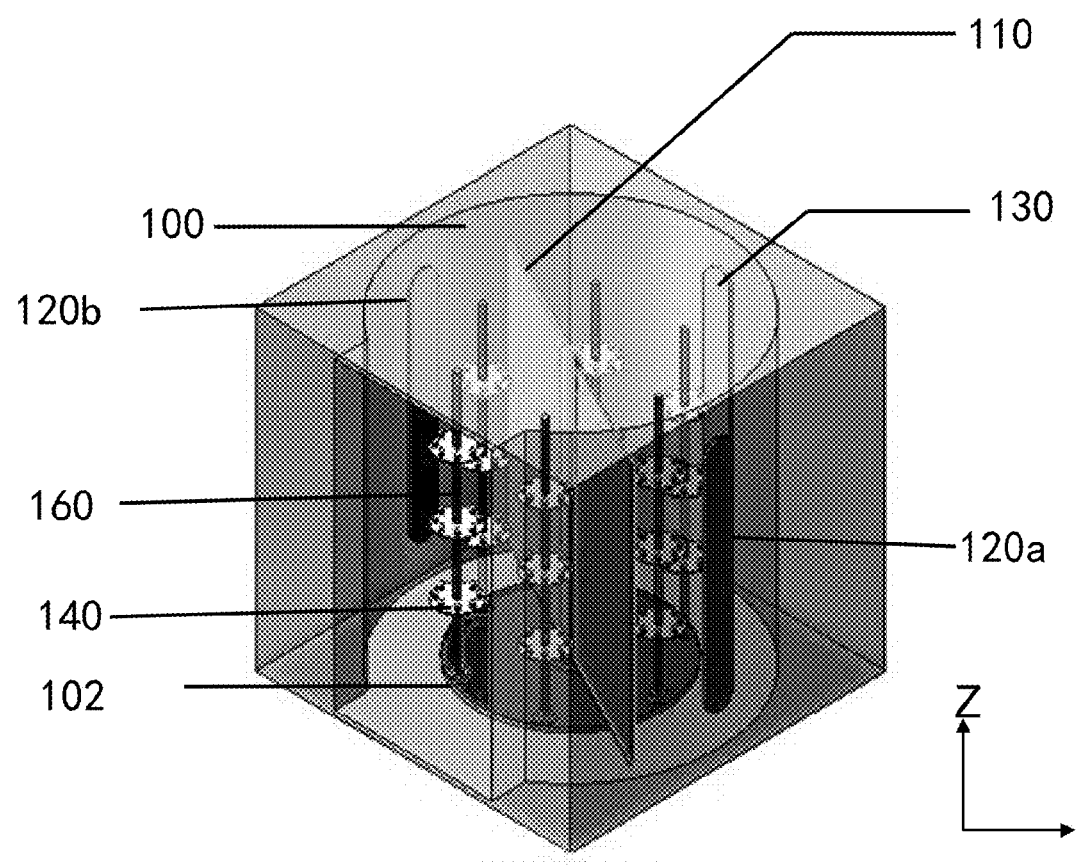
FIG. 1 is a stereoscopic schematic view of a magnetron sputtering coating device according to an example of the present disclosure.
Figure 2:
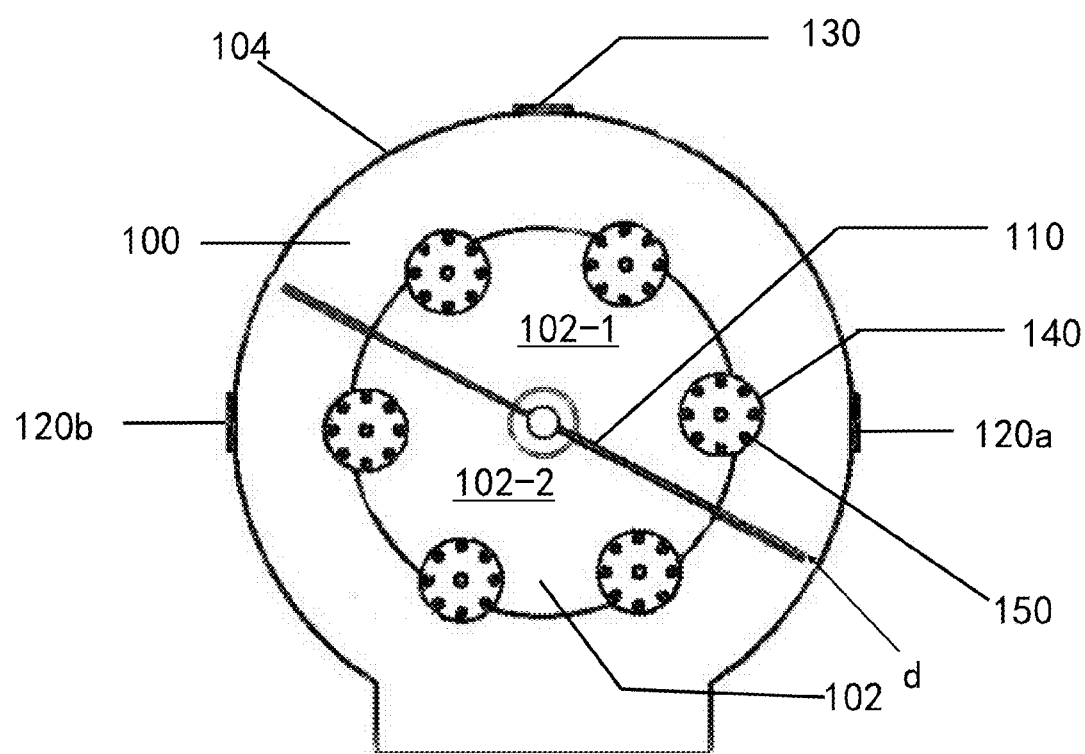
FIG. 2 is a top schematic view of the magnetron sputtering coating device as shown in FIG. 1.

FIG. 1 and FIG. 2 show a stereoscopic and top structural schematic view of a magnetron sputtering coating device according to an example of the present disclosure. According to some embodiments, the magnetron sputtering coating device includes a deposition chamber 100, a rotating stand 102, sputtering cathodes, and a support platform 140, as well as a first rotation system (not shown in the drawing) for driving the rotating stand 102 to rotate around a central axis of the rotating stand. The coating device may further include other suitable parts, for example, a heating device, a temperature control system, a cooling water circulation system, and a power supply system electrically connected with the sputtering cathode (not shown in the drawing).

In some embodiments, the sputtering cathodes include two first sputtering cathodes 120a and 120b and one second sputtering cathode 130, which are arranged on a circumference 104 concentric with the rotating stand 102. The circumference 104 where the sputtering cathodes are located can either be an actual component such as an inner wall of the deposition chamber 100, or a virtual circumference such as any position between the rotating stand 102 and the inter wall of the deposition chamber 100. In some embodiments, the two first sputtering cathodes 120a and 120b may be arranged parallel to each other and at points that equally divide the circumference 104. The second sputtering cathode 130 may be positioned in the middle of cathodes 120a and 120b, such that the second sputtering cathode 130 divides the arc between the two first sputtering cathodes 120a and 120b to two equal parts. The arc between the two first sputtering cathodes 120a and 120b is substantially 180°, while the arc between the second sputtering cathode 130 and the first sputtering cathodes 120a and 120b is substantially 90°. The first sputtering cathodes 120a and 120b can be a sputtering cathode of a certain chemical element. The second sputtering cathode can be a sputtering cathode of another chemical element. The sputtering cathode material can be selected according to a specific product that needs to be coated. For example, the first sputtering cathodes can have a graphite target while the second sputtering cathode can have a titanium target. In some other examples, the first sputtering cathodes can have a graphite target while the second sputtering cathode can have a tantalum target.

Figure 3:
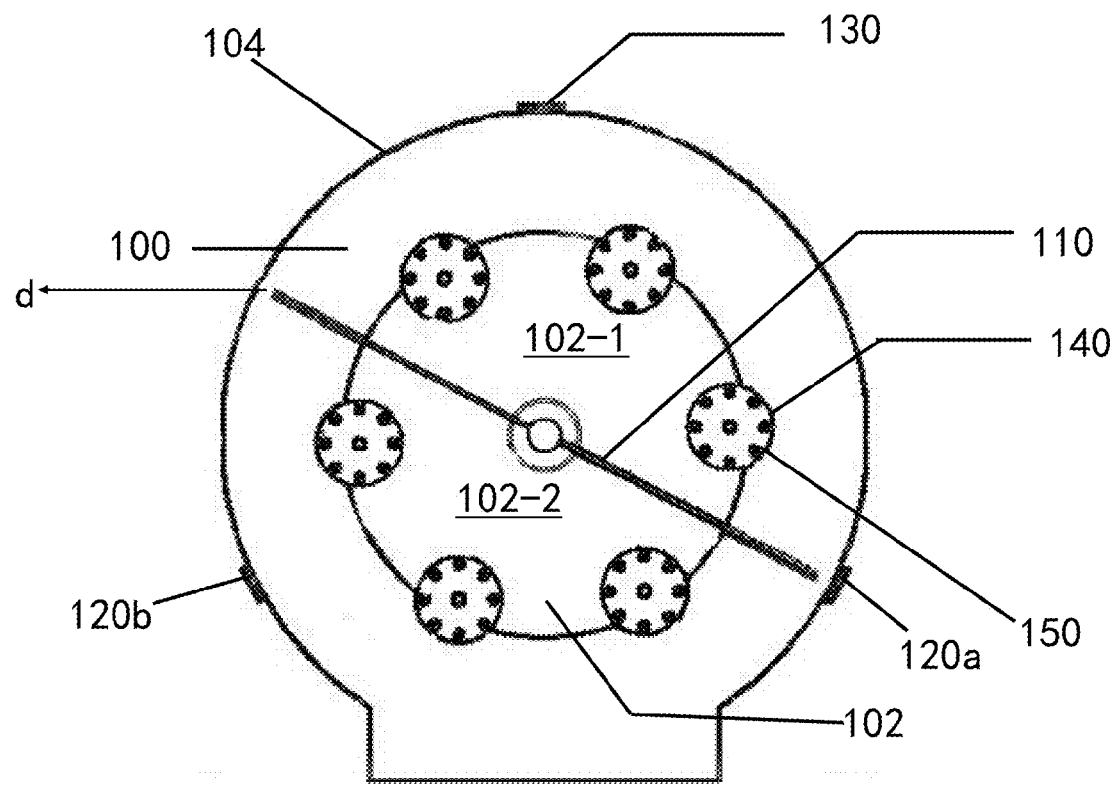
FIG. 3 is a top schematic view of the magnetron sputtering coating device according to another example of the present disclosure.

In some other examples, the two first sputtering cathodes 120a and 120b and the second sputtering cathode 130 can also be arranged on other positions on the circumference 140. For example, the arc between the two first sputtering cathodes 120a and 120b can be any angle ranging from 180° to 240°. The second sputtering cathode 130 can be positioned in the middle of the first sputtering cathodes 120a and 120b. The arc between the second sputtering cathode 130 and the first sputtering cathode 120a/120b can be any angle ranging from 90° to 120°. In the example shown in FIG. 3, the arc between the second sputtering cathode 130 and the first sputtering cathodes 120a and 120b is 120°.

In some embodiments, the rotating stand 102 may be a circular platform. The device may also include a baffle 110 fixed on the rotating stand 102. The baffle 110, which may be a plate, can be made from titanium, aluminum, stainless steel and the like or a combination thereof. As shown in FIG. 1, the baffle 110 is positioned along a diameter of the rotating stand 102 and is arranged perpendicular to the rotating stand 102. The baffle 110 divides the rotating stand 102 into two mutually independent areas 102-1 and 102-2. In some embodiments, both ends of the baffle 110, in the direction perpendicular to the rotating stand (the direction of the Z axis), are beyond both ends of the sputtering cathodes 120a, 120b and 130. The baffle 110 blocks one or more of the sputtering cathodes 120a, 120b and 130 in a certain area, and allows the coating of certain sputtering cathodes in the opposing area. In order to achieve a better blocking effect, the baffle 110 may have a width bigger than the diameter of the rotating stand 102, where the width refers to the length of the baffle along the diameter of the rotating stand 102. In some embodiments, the distance "d" between the baffle 110 and a closest point on the circumference of the support platform 140 where the sputtering cathode is located is 2-10 cm.

The rotating stand 102 may be provided with a first rotation system (not shown in the drawing) for driving the rotating stand 102 to rotate around a central axis of the rotating stand 102. The rotating stand 102 and the baffle 110 can both rotate around the central axis of the rotating stand 102. When the rotating stand 102 rotates to a position, e.g. the position as shown in FIG. 2, with the blocking of the baffle 110, an area 102-1 of the rotating stand 102 is exposed to the first sputtering cathode 120a (e.g., the graphite target) and the second sputtering cathode 130 (the titanium target), allowing the product (or the substrate) to be coated in the area 102-1 to be coated with a film of carbon: titanium carbide (a mixed layer of carbon with titanium carbide); while another area 102-2 of the rotating stand is exposed to the first sputtering cathode 120b (the graphite target), thus allowing the product in the area 102-2 to be coated with a carbon film. With the rotation of the rotating stand 102, the product in different areas will be coated alternately with the carbon: titanium carbide film and the carbon film, thus realizing the coating of the product with a nano-multilayer film. The thickness of a single layer can be controlled by adjustment of the rotational speed of the rotating stand.

In some other examples, the baffle 110 can also be placed at other positions on the rotating stand 102, but not necessarily along the diameter. The baffle 110 may be a bent plate or any other shape that divides the rotating stand 102 into two separate areas.

The device may further include a second rotation system for driving the support platform 140 to rotate around the central axis of the support platform 140. As shown in FIG. 1, multiple support platforms 140 can be arranged on the rotating stand 102 on a support rod 160. The support platforms 140 can be positioned at intervals on the same support rod 160. The support platform 140 is used to support the substrate (or product) 150 to be processed, which can be uniformly arranged on the circumference of the support platform 140. With the rotation of the support platform 140 around its axis, the coating on each of the products to be coated on the support platform 140 can be uniform.

In some other embodiments, four sputtering cathodes (not shown in the drawing) can be used around the rotating stand 102. The sputtering cathodes can include two first sputtering cathodes and two second sputtering cathodes. The two first sputtering cathodes can be arranged opposite to each other, and the two second sputtering cathodes can be arranged opposite to each other. The four sputtering cathodes can be arranged at equal intervals on a circumference. In some embodiments, during the preparation of the multilayer film, one of the second sputtering cathodes can be kept idle. The corresponding parameters such as the target current and voltage may be set for the two first sputtering cathodes and one of the second sputtering cathodes instead of for the other second sputtering cathode, which is not used for sputtering and in an idle state. In the example, although four sputtering cathodes are arranged, they may not be used for sputtering at the same time.

The substrate to be coated can either be human implantation equipment such as a bone articular head or acetabular cup, or be other substrates such as engineering items. The substrate can be made of metal or alloy materials or other materials.

The present disclosure also provides a method of coating a substrate using the above-described magnetron sputtering coating devices. According to some embodiments, the method may include a first, second, and third sputtering stage. In the first sputtering stage, a working current of two first sputtering cathodes may be set to 0. A second sputtering cathode is set to have a working current of a first predetermined current value and to be at a constant voltage mode. The working bias voltage is kept at a first predetermined bias voltage and then the sputtering of a first predetermined duration is performed. Then, all sputtering cathodes are set to be at a constant voltage mode, and the working bias voltage is kept at a second predetermined bias voltage. The working current of the two first sputtering cathodes, starting from an initial working current I1, is increased by ΔI1 at intervals of a first time interval T1, until reaching a second predetermined current value; the working current of the second sputtering cathode, starting from the first predetermined current value, is decreased by ΔI2 at intervals of a second time interval T2, until reaching a third predetermined current value.

In the second sputtering stage, all sputtering cathodes are set to be at a constant voltage mode, and the working bias voltage is kept at the second predetermined bias voltage. The working current of the second sputtering cathode is set to and kept at a fourth predetermined current value, and the working current of the first sputtering cathode is kept at the second predetermined current value or is set to and kept at a fifth predetermined current value, and then the sputtering of a second predetermined duration is performed.

In the third sputtering stage, the working bias voltage is kept at the second predetermined bias voltage, the working current and voltage of the second sputtering cathode are set to be zero, and the first sputtering cathode is kept at the working current of the second sputtering stage or is set to and kept at a sixth predetermined current value, and is kept at the constant voltage mode, and then the sputtering of a third predetermined duration is performed.

In some embodiments, a method for sputtering may use three sputtering cathodes, i.e., two first sputtering cathodes and one second sputtering cathode. In some other embodiments, another second sputtering cathode may be used. Alternatively, the second sputtering cathode may be kept in an idle state and kept from being used in the preparation of the nano-multilayer film.

In some examples, the first sputtering cathodes of the magnetron sputtering coating device are titanium targets, and the second sputtering cathode is a titanium target. First, the substrate to be coated (or the product to be coated) is put on the support platform 140 in the deposition chamber 100. The deposition chamber 100 is vacuumed to $2 \times 10^{-4}$ Pa, with high pure argon introduced at a flow of 25 sccm. Then, the sputtering cathodes can be cleaned, and all the sputtering cathodes can be applied with a current of 0.4 A and a voltage of 500 V for 20 minutes for cleaning.

The sputtering can then be performed. During the whole sputtering process, with the rotating stand 102 rotating at a constant speed, the substrate to be coated can also be rotated. More specifically, in a first sputtering stage, the first predetermined current value of the second sputtering cathode can be set at 3.0-7.0 A, the voltage of the second sputtering cathode can be set at 800V. The first predetermined bias voltage is 100-200V, and the first predetermined duration is 5-15 min. The working bias voltage can be set at the second predetermined value of 60-130V, wherein, the two first sputtering cathodes can be set at the initial working current I1 of 0.5-2.0 A. For the two first sputtering cathodes, at a time interval of, for example, 5-15 min, their working current is increased by a certain value, for example, 0.5-1.5 A, until their working current is increased to a predetermined value, for example, 4.0-7.0 A. For the second sputtering cathode, at a time interval of 5-15 min, its working current is decreased by a certain value, for example, 0.5-1.5 A, until its working current is decreased to a predetermined value such as 0-3.0 A. That is, during the sputtering process of the first stage, the current of the first sputtering cathode is increased, e.g., stepwise, and the current of the second sputtering cathode is decreased, e.g., stepwise. The increase amount at each step and the decrease amount at each step may be the same or different. The time intervals for each step for the first sputtering cathodes and the second sputtering cathode may be the same or different. The voltages for the first sputtering cathodes and the second sputtering cathode may be kept constant in the whole process. After a period of sputtering, such as for 50-100 min, the transition layer of 300-500 nm in thickness composed of titanium film and a mixed layer of TiC and quasi-graphite can be deposited onto the product, which can be a metal material. Because the current gradients of different targets are controlled in the process as described above, the mass percentage of Ti in the transition layer, from a layer in proximity to the metal material layer of the product to an upper layer, is decreased gradually from a higher percentage to a lower percentage. The mass percentage of C is increased gradually from a lower percentage. Thus, the binding force with the substrate, especially the substrates of metal or alloy materials, is increased, and also its lubricity is increased gradually.

The mixed layer of titanium carbide and quasi-graphite refers to a layer of titanium carbide mixed with the quasi-graphite. That is, the mixed layer contains both quasi-graphite and titanium carbide.

In the second sputtering stage, the working current of the first sputtering cathode can be kept at 4.0-7.0 A, which is the last predetermined value of the first sputtering stage. The working current of the first sputtering cathode can also be set and kept at a desired predetermined value such as 4.0-7.0 A. Meanwhile, the working current of the second sputtering cathode is set and kept at a desired predetermined value such as 0.5-2.0 A. The voltage of all sputtering cathodes can be kept at a constant voltage of 800V. Sputtering can be performed for 120-400 min, during which the working bias voltage is kept constant of the second predetermined bias voltage. Under these processing conditions, a composite layer of 1600-3300 nm is formed, which is a multilayer structure with the quasi-graphite layer (the content of $sp^2$ is about 60%) and the diamond-like carbon layer (the content of $sp^3$ is about 70%) alternately laminated.

In the third sputtering stage, the working bias voltage is kept at constant of the second predetermined bias voltage. The voltage and current of the second sputtering cathode are decreased to 0, making it idle, and the current of the two first sputtering cathodes is reset to a desired predetermined value such as 4.0-7.0 A. The current of the the two first sputtering cathodes can also be kept at the current of the second sputtering stage. The voltage of the two first sputtering cathodes is kept at a constant voltage of 800V. At this stage, sputtering is performed for 15-20 min. Under these processing conditions, a diamond-like carbon top-layer film of about 100 nm is separately formed on the composite layer. The quasi-diamond of a high hardness makes the nano-multilayer film have better hardness and wear resistance. At this stage, a nano-multilayer film in combination with the substrate is formed. The mass percentage of C in the formed nano-multilayer film is 70%-97.6%, and the mass percentage of Ti is 2.4%-30%.

Figure 4:
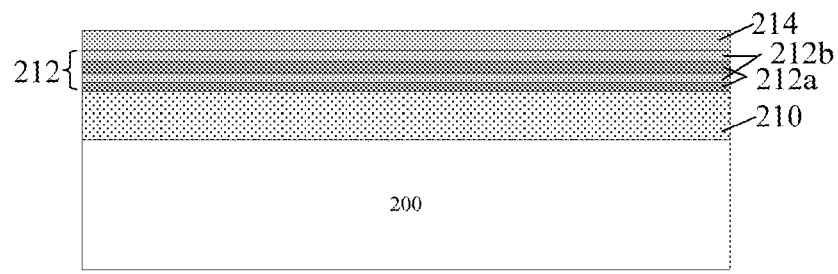
FIG. 4 is a sectional schematic view of a nano-multilayer film in combination with a metal material according to an example of the present disclosure.

Furthermore, the present disclosure further provides a nano-multilayer film formed by the above-described method with the above-described device, as shown in FIG. 4. The nano-multilayer film includes a transition layer 210 including a Ti film and a mixed layer of TiC and quasi-graphite on the substrate 200, a composite layer 212 of alternately laminated diamond-like carbon and quasi-graphite on the transition layer 210, and a diamond-like carbon top-layer film 214 on the composite layer 212. The content of $sp^2$ in the quasi-graphite layer is 60% and the content of $sp^3$ in the diamond-like carbon layer is 70%. In the direction from the substrate 200 to the diamond-like carbon top-layer film 214, the mass percentage of Ti in the mixed layer is gradually decreased, while the mass percentage of C is gradually increased. The composite layer 212 includes a multilayer structure with the quasi-graphite layer 212a and the diamond-like carbon layer 212b alternately laminated. There can be no limit to the number of the quasi-graphite layer and the diamond-like carbon layer in the composite layer 212. The interface of the nano-multilayer film where the transition layer is in combination with the substrate contains higher content of titanium and lower content of carbon, thus having a higher binding force with the substrate, also having a low internal stress and good lubricity. Thus, the hardness and wear resistance are improved through the diamond-like carbon top-layer.

In a specific example 1, the two first sputtering cathodes include graphite targets, while the one second sputtering cathode includes a titanium target. The arc between the second sputtering cathode and one of the first sputtering cathodes in the sputtering device is substantially of 90°, the rotating stand has a rotational speed of 1.5 rpm, and the substrate to be coated is rotated on its axis. All the sputtering cathodes are applied with a current of 0.4 A and a voltage of 500 V for 20 minutes of sputter cleaning. Before coating, the substrate to be coated is put onto the supporting platform of the deposition chamber, and the deposition chamber is vacuumed to $2\times10^{-4}$ Pa, with the high pure argon introduced at a flow of 25 sccm. Then the sputtering is performed. Working bias voltage is set to 150V. One titanium target is set to have a constant voltage of 800V and a current of 7.0 A, and sputtering of 10 min is performed; then, working bias voltage is decreased to 100V. The titanium target is kept at the constant voltage of 800V and has a current decreased stepwise by 1.0 A at intervals of 10 min until down to 0. The two graphite targets are set to have a constant voltage of 800V and a working current starting from 1.5 A and increased stepwise by 1.0 A at intervals of 10 min until up to 7.0 A. After sputtering for 60 min, a transition layer composed of titanium film and a mixed layer of TiC and quasi-graphite (the ratio of C of the mixed layer is increased gradually, while the ratio of Ti is decreased gradually) of about 300 nm is deposited onto the substrate. And then, with the current and voltage of the two graphite targets kept constant, the current of the titanium target is increased to 1.0 A, with the voltage kept at a constant voltage, the working bias voltage is kept at 100 V. After 120 min, a composite layer of 1600 nm is formed on the transition layer, comprising a quasi-graphite layer (the content of $sp^2$ is about 60%) and a diamond-like carbon layer (the content of $sp^3$ is about 70%) alternately laminated. The current and voltage of the titanium target can be then decreased to 0, and the current of the graphite target is increased to 7.0 A, with the voltage kept at 800 V. The working bias is kept at 100V. After 15 min, a diamond-like carbon film of 100 nm is formed on the composite layer. In the example, the mass percentage of C in the formed nano-multilayer film is about 97%, and the mass percentage of Ti is about 3%.

In another specific example 2, the two first sputtering cathodes in the sputtering device are graphite targets, and the one second sputtering cathode is a titanium target. The arc between the second sputtering cathode and the first sputtering cathode is substantially of 90°, the rotating stand has a rotational speed of 2.0 rpm, and the substrate to be coated is rotated on its axis. Before coating, the substrate to be coated is put onto the support platform of the deposition chamber, and the deposition chamber is vacuumed to $2\times10^{-4}$ Pa, with the high pure argon introduced at a flow of 25 sccm. The sputtering cathodes are applied with a current of 0.4 A and a voltage of 500 V for 20 minutes of sputter cleaning. Then, the sputtering is performed. The working bias voltage is set to 120V. One titanium target is set to have a constant voltage of 800V and a current of 6.5 A, and sputtering of 5 min is performed. The working bias voltage can then be decreased to 110V, and the titanium target is kept at the constant voltage of 800V and has a current decreased stepwise by 1.0 A at intervals of 5 min until down to 0. The two graphite targets being set to have a constant voltage of 800V and a working current starting from 0.8 A and increased stepwise by 1.0 A at intervals of 5 min until up to 6.5 A; After 80 min, a transition layer composed of titanium film and a mixed layer of TiC and quasi-graphite (the ratio of C of the mixed layer is increased gradually, while the ratio of Ti is decreased gradually) of about 400 nm are deposited onto the substrate. With the current and voltage of the two graphite targets kept constant, the current of the titanium target is increased to 1.5 A, with the voltage kept at the constant voltage. The working bias voltage is kept 110 V. After 180 min, a composite layer of 1800 nm is formed on the transition layer, comprising the quasi-graphite layer (the content of $sp^2$ is about 60%) and the diamond-like carbon layer (the content of $sp^3$ is about 70%) alternately laminated. Then, the current and voltage of the titanium target are decreased to 0. The current of the graphite target is increased to 6.5 A, with the voltage kept at 800 V, and the working bias being kept at 110V. After 15 min, a diamond-like carbon film of 100 nm is formed on the composite layer. In the example, the mass percentage of C in the formed nano-multilayer film is about 92%, and the mass percentage of Ti is about 8%.

In still another specific example 3, the two first sputtering cathodes in the sputtering device are the graphite targets, while the one second sputtering cathode is a titanium target. The arc between the second sputtering cathode and the first sputtering cathode is substantially of 90°, the rotating stand has a rotational speed of 2.5 rpm, and the substrate to be coated is rotated on its axis. Before coating, the substrate to be coated is put onto the support platform of the deposition chamber, and the deposition chamber is vacuumed to $2\times10^{-4}$ Pa, with the high pure argon introduced at a flow of 25 sccm. All the sputtering cathodes are applied with a current of 0.4 A and a voltage of 500 V for 20 minutes of sputter cleaning. The sputtering is performed. The working bias voltage is set to 150V. One titanium target is set to have a constant voltage of 800V and a current of 6.0 A, and sputtering of 12 min is performed. The working bias voltage can then be decreased to 120V. The titanium target is kept at a constant voltage of 800V and has a current decreased stepwise by 1.0 A at intervals of 12 min until down to 0. The two graphite targets are set to have a constant voltage of 800V and a working current starting from 1.8 A and increased stepwise by 1.0 A at intervals of 12 min until up to 6.0 A. After 100 min, a transition layer composed of titanium film and a mixed layer of TiC and quasi-graphite (the ratio of C of the mixed layer is increased gradually, while the ratio of Ti is decreased gradually) of about 500 nm are deposited onto the substrate. Then, with the current and voltage of the two graphite targets kept constant, the current of the titanium target is increased to 1.8 A, with the voltage kept at a constant voltage. The working bias voltage is kept at 120 V. After 260 min, a composite layer of 1900 nm is formed on the transition layer, comprising the quasi-graphite layer (the content of $sp^2$ is about 60%) and the diamond-like carbon layer (the content of $sp^3$ is about 70%) alternately laminated. Then, the current and voltage of the titanium target are decreased to 0. The current of the graphite target is increased to 6.0 A, with the voltage kept at 800 V. The working bias is kept at 120V. After 15 min, a diamond-like carbon film of 100 nm is formed on the composite layer. In the example, the mass percentage of C in the formed nano-multilayer film is about 86%, and the mass percentage of Ti is about 14%.

An observation was made to the surface of the nano-multilayer film of the above specific examples 1-3 through a scanning electron microscope, finding that the surface of the nano-multilayer films had small surface roughness. The hardness of the nano-multilayer films was measured by a nanoindentation instrument, with a load of 10 mN, a pressed depth being greater than 10 times of the surface roughness and smaller than 1/10 of the thickness of the nano-multilayer films, so as to guarantee the authenticity and validity of the measured hardness. The longitudinal binding force and the lateral binding force of the nano-multilayer films were evaluated through a standard indentation instrument and the automatic scratch test. With a load of the indentation test being 150 N and the radius of the indenter being 0.2 mm, no crack and delamination was found around the indentation, indicating that the nano-multilayer film had a high longitudinal binding force. The load was increased gradually from 10 N to 85 N, with a sliding velocity of 10 mm/min. There was no crack and peeling around and at the edge of the scratch, indicating that the nano-multilayer film had a high lateral binding force.

The ball-disc friction and wear machine were used for determination of the friction and wear properties of the nano-multilayer film. The grinding ball was a $Si_3N_4$ ceramic ball having a hardness of 1500 HV and a diameter of 3 mm. The load was 10 N, the sliding velocity was 0.10 m/s, and the friction duration was 30 min. The experiments were made under the conditions of room temperature, no lubrication, and humid air (50% relative humidity). In the testing process, the change of the friction coefficient was automatically recorded. After the test, the wear volume was measured with a step meter, with the wear rate calculated. Table 1 shows the hardness, average friction coefficient and wear rate of the nano-multilayer film of Examples 1, 2 and 3.

TABLE 1

| Nano-multilayer film | Content of Ti (at. %) | Sectional binding force of nano-multilayer film with substrate (N) | | Average friction coefficient (u) | Wear rate ($m^3$/Nm) |
| --- | --- | --- | --- | --- | --- |
| | | Longitudinal | Lateral | | |
| Example 1 | 3 | >150 | ≥95 | 0.048 | $2.8 \times 10^{-17}$ |
| Example 2 | 8 | >150 | ≥95 | 0.052 | $2.3 \times 10^{-17}$ |
| Example 3 | 14 | >150 | ≥95 | 0.046 | $3.1 \times 10^{-17}$ |

The nano-multilayer film of the present invention has a low friction coefficient, a high wear resistance and a high bonding force with the substrate of the product. In the nano-multilayer film of the specific examples 1, 2 and 3, the average friction coefficients of their films are 0.048, 0.052 and 0.046, respectively, without obvious change of the friction coefficient during the test process, indicating that the nano-multilayer film has a good friction stability, the surface wear trace of the nano-multilayer film being very shallow after the wear. The wear rates of the nano-multilayer films of the specific examples 1, 2 and 3 are $2.8 \times 10^{-17}$, $2.3 \times 10^{-17}$ and $3.1 \times 10^{-17}$ $m^3$/Nm, respectively, indicating that the nano-multilayer film has a good wear resistance. Moreover, the pits of the nano-multilayer films of the specific examples 1, 2 and 3 formed under the load of 150 N have no crack, delamination or peeling trace at the edge thereof. Under the load of 85 N, there is no crack or peeling of the nano-multilayer film observed in the area and at the edge of the scratch formed on the surface of the nano-multilayer film. The pit and scratch tests show that the nano-multilayer film has excellent bonding strength with the metal substrate.

What is described above is only the preferred embodiments of the present invention. It should be pointed out that, for those of ordinary skill in the art, some improvements and amendments can further be made under the premise of not departing from the principles of the present invention, and should also be regarded as being within the scope of protection of the present invention.

What is claimed is:

1. A magnetron sputtering coating device, comprising:
   a deposition chamber;
   a rotating stand positioned within the deposition chamber and having a rotating axis;
   two first sputtering cathodes and a second sputtering cathode located on a circumference concentric with the rotating axis, wherein the second sputtering cathode contains a material different from the two first sputtering cathodes; and
   a baffle fixed on the rotating stand and divides the deposition chamber into at least two areas, wherein at least one first sputtering cathode is in one area, the second sputtering cathode is in another area, and at least one of the at least two areas includes one of the first and second sputtering cathodes and at least a part of the other of the first and second sputtering cathodes.

2. The magnetron sputtering coating device according to claim 1, wherein the first sputtering cathodes each include a graphite target, and the second sputtering cathode includes a titanium or tantalum target.

3. The magnetron sputtering coating device according to claim 1, wherein the baffle extends along a diameter of the rotating stand.

4. The magnetron sputtering coating device according to claim 1, wherein the two first sputtering cathodes form an arc of substantially 180°-240° therebetween, and the second sputtering cathode is positioned substantially in the middle of the two first sputtering cathodes.

5. The magnetron sputtering coating device according to claim 1, wherein the baffle is made of titanium, aluminum, stainless steel, or a combination thereof.

6. The magnetron sputtering coating device according to claim 1, further comprising a support platform on the rotating stand for supporting an article to be coated.

7. The magnetron sputtering coating device according to claim 6, further comprising a rotation system for rotating the support platform around a central axis of the support platform.

8. The magnetron sputtering coating device according to claim 1, further comprising multiple support platforms arranged on a support rod on the rotating stand.

9. The magnetron sputtering coating device according to claim 1, wherein the sputtering cathodes are arranged on an inner wall of the deposition chamber.

10. The magnetron sputtering coating device according to claim 1, wherein the two first sputtering cathodes are positioned opposite to each other, and the device further includes another second sputtering cathode arranged opposite to the second sputtering cathode.

* * * * *